United States Patent [19]

Marquardt et al.

[11] Patent Number: 5,120,535
[45] Date of Patent: Jun. 9, 1992

[54] ONCOSTATIN M AND NOVEL COMPOSITIONS HAVING ANTI-NEOPLASTIC ACTIVITY

[75] Inventors: Hans Marquardt, Mercer Island; Joyce M. Zarling, Seattle; Mohammed Shoyab, Seattle; Marcia B. Hanson, Seattle; Mario N. Lioubin, Bellevue; Thomas J. Brown, Seattle, all of Wash.; Tatsuhiko Ikeda, Kobe, Japan

[73] Assignee: Oncogen, Seattle, Wash.

[21] Appl. No.: 46,846

[22] Filed: May 4, 1987

Related U.S. Application Data

[63] Continuation-in-part of Ser. No. 935,283, Nov. 26, 1986, abandoned, which is a continuation-in-part of Ser. No. 811,235, Dec. 20, 1985, abandoned.

[51] Int. Cl.$^5$ .................. A61K 37/02; A61K 37/66; A61K 45/05
[52] U.S. Cl. .................. 424/85.5; 424/85.1; 424/85.4; 514/2; 514/21; 435/240.2; 435/240.3
[58] Field of Search .................. 424/85.5, 85.4, 101, 424/85.1, 534, 529; 514/2, 21, 885; 435/70.4, 70.5, 70.1, 240.1, 240.2, 948, 811; 530/351, 399, 397, 829, 837, 838, 828

[56] References Cited

U.S. PATENT DOCUMENTS 4,737,580 4/1988 Twardzik et al. .................. 530/388

FOREIGN PATENT DOCUMENTS

0169016A2 8/1985 European Pat. Off. .

OTHER PUBLICATIONS

Lee et al., *J. of Imm.* 133:3, 1083–1086, 1984, "The Synergistic Proliferative Effect of Interferon & Human Lumpotoxin".

Amento et al., *PNAS*, 79: 5307–5311, 1982, "Modulation of synovial cell products by a factor from a human cell line T lymphocyte induction of a mononuclear cell factor".

Aggawal et al., *JBC* 259, 686–691, 1984, Human Lymphotoxin.

Sporn et al., *NEJM*, Oct. 1980, 878–880, "Autocrine Secretion and Malignant Transformation of Cells".

Ciba Foundation Symposium 116, Burgess, "Medical Aspects of Growth Factors", p. 261, Ciba Foundation, Oct. 1985.

Larry Ellingsworth et al., *Journal of Biological Chemistry*, "Anti-Bodies to the N-Terminal Portion of Cartilage-Inducing Factor A & Transforming Growth Factor-β" (1986) 261: 12362–12367.

Saeid Seyedin et al., *Proc. Natl. Acad. Sci. U.S.A.*, "Purification and characterization of two cartilage-inducing factors from bovine demineralized bone", (1985) 82: 2267–2271.

Saeid Seyedin et al., *J. Biol. Chem.*, "Cartilage-Inducing Factor-β is a Unique Protein Structurally and Functionally Related to Transforming Growth Factor-β", (1987) 260: 1946–1949.

*Primary Examiner*—Elizabeth C. Weimar
*Assistant Examiner*—Gail Poulos
*Attorney, Agent, or Firm*—Pennie & Edmonds

[57] ABSTRACT

Novel compositions are provided for modulating growth, particularly of tumor cells, which compositions are combinations of Oncostatin M, and one or both of transforming growth factors or γ-interferons, or analogs thereof. In addition, a novel transforming growth factor is provided, designated TGF-β2, as well as methods for its preparation.

2 Claims, No Drawings

ONCOSTATIN M AND NOVEL COMPOSITIONS HAVING ANTI-NEOPLASTIC ACTIVITY

CROSS-REFERENCED RELATED APPLICATIONS

This application is a continuation-in-part of application Ser. No. 935,283, filed Nov. 26, 1983, now abandoned, which is a continuation-in-part of application Ser. No. 911,235, now abandoned, filed Dec. 20, 1983 which applications are incorporated herein by reference.

TECHNICAL FIELD

Cell growth regulatory compositions are disclosed, where the compounds work independently and provide for synergistic effects in combination.

BACKGROUND

There is a continuing and increasing understanding of the manner in which the growth of a cell in vivo is regulated. Much attention has been directed toward the isolation of growth regulatory polypetides from activated leukocytes. Of particular interest are those polypeptides which selectively inhibit the growth of neoplastic cells while not inhibiting the growth of surrounding normal tissue. Interferons (IFN) have shown growth inhibitory activity against a variety of tumor cells. There has also been reported synergy between low levels of different types of IFN or of IFN and other growth inhibiting peptides, such as lymphocyte-derived tumor necrosis factor-$\beta$(TNF-$\beta$). TNF-$\beta$ as well as TNF-$\alpha$, derived from myelocytic cells, displayed cytostatic and/or cytocidal activity against several transformed cell lines, but normal cells were unaffected. TGF-$\beta$ is produced and released by a variety of cells, including T-cells and monocytes, and can both stimulate and inhibit cell proliferation, depending largely on the cell type. TNFs and TGF-$\beta$s are produced by both activated macrophages and T-lymphocytes, and are structurally and functionally conserved among different species and cell types of the immune system.

Other compounds have also been reported as having selective activity against neoplastic cells. Since there is substantial interest in being able to control tumor cell growth, the ability to regulate tumor cell growth is of great interest. However, the naturally occurring compounds usually have a broad range of activities toward different cells and at concentrations which may be effective in inhibiting the growth of neoplastic cells, frequently demonstrate undesired effects toward normal cells. There is, therefore, substantial interest in being able to develop compositions which may be employed at low concentrations when administered therapeutically, while still providing the desired growth inhibitory effects, and with minimal deleterious effects on the normal cells.

RELEVANT LITERATURE

A review of the family of compounds under the designation TGF-$\beta$ is provided by Sporn et al., *Science* (1986) 233:532-534. The structure and functional relationship with CIF-B (cartilage-inducing factor B) to TGF-$\beta$ is demonstrated by Seydin et al., *J. Biol. Chem.* (1987) 262:1946-1949. See also Seydin et al., *Proc. Natl. Acad. Sci. USA* (1985) 82:2267-2271.

Procedures for purification of growth inhibitor compounds have been described by Henderson et al., *J. Immunol* (1983) 131:810-815 and Marquardt and Todaro, *J. Biol. Chem.* (1982) 257:5220-5225.

Synergy between low levels of different types of IFN or IFN and other growth inhibiting peptides like tumor necrosis factor-$\beta$ are described by Lee et al., *J. Immunol.* (1984) 133:1083-1086. The effects of TNF-$\beta$ and TNF-$\alpha$ are described by Sugarman et al., *Science* (1985) 230:943-945. Oncostatin M, its purification and characterization, are described by Zarling et al., *Proc. Natl. Acad. Sci. USA* (1986) 83:9739-9743.

SUMMARY OF THE INVENTION

Novel anti-neoplastic compositions and their use are provided, where the compositions are combinations of at least two agents, where one of the agents is Oncostatin M. The combinations are found to have good synergy in requiring substantially lower concentrations of the individual components for producing the anti-proliferation effect on neoplastic cells, than would be predicted from the anti-neoplastic activity of the individual components. A novel transforming growth factor-$\beta$ is provided designated TGF-$\beta$2.

DESCRIPTION OF THE SPECIFIC EMBODIMENTS

Novel anti-neoplastic compositions are provided having at least two components, where one of the components is Oncostatin M or an analog thereof. Oncostatin M is also characterized as being produced by a phorbol ester activated histiocytic lymphoma cell line, U937, with resulting differentiation into macrophage-like cells. Oncostatin M is also isolated from the acid-soluble fraction of T-cell-conditioned medium. Oncostatin M has a molecular weight of about 28 kD and is able to inhibit A375 human melanoma cell proliferation.

Oncostatin M will include the following amino acid sequence:

$$A\text{-}A\text{-}I\text{-}G\text{-}X\text{-}X\text{-}X\text{-}K\text{-}E\text{-}Y\text{-}X\text{-}V\text{-}L\text{-}X\text{-}X\text{-}Q\text{-}L\text{-}Q\text{-}K$$

(where X intends the amino acid is not designated.)

Oncostatin M finds use with other growth regulatory proteins, particularly those produced by lymphocytes, more particularly those factors which have substantial homology with, that is greater than at least about 70%, preferably greater than at least about 90%, of $\gamma$-Interferons and transforming growth factors, more particularly the transforming growth factors-$\beta$, both one and two, or active fragments thereof.

In culture, the various components of the anti-neoplastic composition may be derived from any vertebrate source, not necessarily the same source as the cells. However, for treatment of a mammal, it will usually be desirable to employ a component which has substantially the same or the same sequence as the naturally occurring component, so as to minimize the potential for an immunogenic response. Usually, the component will differ by fewer than 5 mole percent, more usually by fewer than 2 mole percent from the amino acid sequence of the naturally occurring sequence from the host.

The composition may have two or more components, usually having fewer than six components, directed to anti-neoplastic activity. Besides the Oncostatin M which will usually be present in from about 10, usually at least 25 weight percent, and not more than about 90, usually not more than about 80 weight percent of the inhibiting components, one or more TGFs may be employed, as well as one or more γ-IFNs may be employed. Thus in particular situations, it may be desirable to use mixtures of related compositions, rather than an individual compound. As already indicated, besides the naturally occurring compounds, active fragments may be employed, as well as chimeras, where a portion of one related molecule is joined to the other portion of another related molecule. See, for example, EPA 32,134 and corresponding U.S. application Ser. No. 791,247, filed Oct. 25, 1985.

The various components may be obtained in a variety of ways. The subject components are available from naturally occurring sources, particularly conditioned media, where the individual components may be purified employing various purification techniques. These techniques may include solvent extraction, gel permeation chromatography, reversed phase-HPLC, electrophoresis, or the like. For smaller molecules, various synthetic techniques may be employed, where the polypeptide will be synthesized on a solid support. A number of commercial synthesizers are available and may be used to advantage, for example, from Smith Kline, Beckman, Applied Biosystems, etc. Finally, recombinant techniques may be employed where a sequence coding for the particular component or active fragment thereof may be introduced into an expression cassette, which may then be transformed into an appropriate host. Either prokaryotic or eukaryotic hosts may be employed, which may include bacteria, yeast, mammalian cells, e.g. CHO cells, monkey kidney cells, etc. The particular techniques for isolating or preparing sequences, constructing an expression cassette, transforming the expression cassette into a host, where the expression cassette may be maintained on an extrachromosomal element or integrated into the chromosome of the host, and expression and isolation of the polypeptide product, finds ample exemplification in the literature and need not be expanded upon here. See, for example, U.S. Pat. No(s). 4,530,901; 4,551,433; 4,569,790; 4,582,800; and 4,615,974.

The resulting products may be glycosylated or nonglycosylated, having the wild-type or other glycosylation. In addition, the sequence may differ by not more than about 5 mole percent, usually by not more than about 2 mole percent from the wild-type sequence of interest.

The composition will vary widely depending upon its intended purpose, the desired ratio of the components, as well as the nature of the components and their activity. Thus, depending upon the nature of the cell line, its response to the different components and their synergistic activity, the ratios of the various components will vary. Usually, the amount of Oncostatin M which is employed in combination will be greater than about 0.1% and less than about 50% of the amount of Oncostatin M which would provide the desired activity by itself. For the most part, the amount of Oncostatin M will generally be in the range of about 0.5 to 25% of the amount of Oncostatin M employed by itself. The total amount of TGFs will generally be in the range of about 0.1 to 50% of the amount of TGF employed by itself to achieve the desired activity, usually from about 0.1 to 20%. For the γ-IFN, there is no direct comparison for anti-neoplastic activity. Thus, the amounts of γ-IFN will be based on the level of γ-IFN which provides the desired level of anti-neoplastic inhibition with a predetermined amount of Oncostatin M.

The amounts of Oncostatin M which may be used in culture will generally be in the range of about 1 to 50 growth inhibitor units/ml (see Experimental Section for definition of units). The amounts of TGFs that are employed, will generally be from about 1 to 25 growth inhibitor units/ml (see Experimental Section for definition of units), while the amounts of γ-interferon will generally range from about 1 to 90 growth inhibitor units/ml (see Experimental Section for definition of units). Thus, in culture, one can provide for varying degrees of inhibition in the culture by employing different combinations of the various components with varying types of cells in culture and determining the response of the cells in culture to the different compositions. In this manner, one may define particular combinations which may be used with a mammalian host in the treatment of neoplastic proliferation.

For use in vivo, the subject compositions may be administered in a variety of ways, by injection, by infusion, topically, parenterally, or the like. Administration may be in any physiologically acceptable carrier, such as sterilized water, phosphate buffered saline, saline, aqueous ethanol, etc.

The subject compositions may be formulated in a variety of ways, including in the lumen of liposomes, particularly where the liposomes may be bound to homing molecules targeted for a particular neoplastic cells, e.g. antibodies, indegradable particle matrices, or the like. Other components may be included in the formulation such as buffers, stabilizers, surfactants, biocides, etc. These components have found extensive exemplification in the literature and need not be described in particular here.

The subject compositions may be used in the treatment of a wide variety of neoplastic conditions, such as carcinomas, sarcomas, melanomas, lymphomas, leukemias, which may affect a wide variety of organs, such as the blood, lungs, mammary organ, prostate, intestine, liver, heart, skin, pancreas, brain, etc.

Also provided is a novel transforming growth factor, referred as TGF-β-2 and having the following amino acid sequence:

```
         5              10             15
A—L—D—A—A—Y—C—F—R—N—V—Q—D—N—C 20              25             30
C—L—R—P—L—Y—I—D—F—K—R—D—L—G—W 35              40             45
K—W—I—H—E—P—K—G—Y—N—A—N—F—C—A 50              55             60
G—A—C—P—Y—L—W—S—S—D—T—Q—H—S—R 65              70             75
V—L—S—L—Y—N—T—I—N—P—E—A—S—A—S 80              85             90
P—C—C—V—S—Q—D—L—E—P—L—T—I—L—Y 95             100            105
Y—I—G—K—T—P—K—I—E—Q—L—S—N—M—I

110
V—K—S—C—K—C—S
```

The above sequence is the human sequence. Besides the above sequence, which is a single sub-unit of the dimer, the dimer is also included, as well as fragments thereof. Of particular interest is an amino acid sequence of at least about 8 amino acids in the region from amino acids 1 to 20, more particularly 4 to 15 and within this region, 9 to 14. Also of interest is the C-terminal sequence of amino acids 85 to 112, more particularly 90 to 112. The subject TGF-$\beta$2 finds a wide variety of uses. The TGF-2 may be used as described above, for use as an anti-neoplastic composition. In addition, the subject compositions have growth factor activity with particular types of cells. Thus, the subject composition can be used in cultures to enhance the proliferation of certain cell lines. The composition is provided in at least 60% purity, usually at least 80% purity, preferably at least 95%, and up to complete purity.

Besides being used for its growth inhibiting or activating properties, the subject compositions and fragments thereof may be used in diagnostics. The subject compositions can be used to titrate the number of receptors for TGF-2 on a cell, and as an agonist or antagonist for other growth factors which compete with the subject growth factor for cell receptors. The subject compositions may also be used in competitive assays for detection of TGF-2 in media, particularly physiological media. Thus, the TGF-2 or fragment thereof may be joined to a label, such as a radioisotope, enzyme, fluorescer, chemiluminescer, enzyme fragment, particle, etc. A wide variety of diagnostic assays are known, see, for example, U.S Pat. No(s). 3,791,932: 3,817,837: 4,134,792: 3,996,345.

Also, the subject compounds may be used for the production of antibodies, either polyclonal or monoclonal, where the antibodies may be used for detection of TGF-$\beta$2 in diagnostic assays, for studying the effects of TGF-$\beta$2 on cells in culture, for detecting the presence of TGF-$\beta$2 in conditioned media, and the like.

The subject compositions may be modified by truncating at the N- or C-terminus where up to about 10 amino acids may be removed. However, for biological activity the C-terminus should be retained. In addition, except for the region from about 5 to 15, up to about 5 mole percent of non-conservative mutations may be made and up to 10 mole percent of conservative mutations may be made. For conservative substitutions, the groups may be broken down into non-polar aliphatic amino acids (G,A,P,V,I,L), polar aliphatic amino acids (C,S,T,M,N,Q), aromatic amino acids (F,H,W,Y), basic amino acids (K,R), and acidic amino acids (D,F).

The subject compounds may be prepared by any of the techniques described previously. For example, they may be obtained, by extracting from natural sources, by synthesis, or by recombinant techniques. By recombinant techniques, one may combine the N-terminal portion of TGF-$\beta$2 to the C-terminal portion of TGF-$\beta$1, TGF-$\alpha$, or other growth factor. Thus, chimeric compounds may be prepared with novel activities, which may be substituted for the naturally occurring compounds.

TGF-$\beta$2 may be prepared by employing recombinant techniques. The amino acid sequence may be used to design a prob and a cDNA library or genomic library from stimulated or unstimulated PC3 cells screened for hybridizing sequences. To enhance the likelihood of identifying the correct sequence, a cDNA library from unstimulated prostatic adenocarcinoma cells or other related cell line which does not produce TGF-$\beta$2 may be used to cross-hybridize. Those sequences from the PC3 cells which do not hybridize will be concentrated as to the desired sequence. Sequences which hybridize to the probe and do not cross-hybridize with cDNA from cells which do not produce TGF-2 may be screened by using Xenopus oocytes and employing an assay for the expression of TGF-$\beta$2, by inserting restriction fragments into a prokaryotic expression vector such as $\lambda$gt-11 and screening with antibodies for TGF-$\beta$2 to detect a cross-reactive peptide fragment, or the like. Once the fragment containing the sequence encoding TGF-$\beta$ has been identified, the fragment may be manipulated by resection, primer repair, in vitro mutagenesis, restriction endonuclease digestion, or the like, to provide a different 5' transcriptional and, as appropriate, translational initiation region and optimally a different 3' transcriptional and, as appropriate translation termination region. Various expression vectors are commercially available or described in the literature into which the open reading frame encoding TGF-$\beta$2 may be inserted. The vector may be transformed into an appropriate host for expression. Prokaryotic expression hosts include E. coli and B. subtilis: eukaryotic hosts include S. cerevisiae, CHO cells, monkey kidney cells, streptomyces, etc.

The following examples are offered by way of illustration and not by way of limitation

EXPERIMENTAL

Characterization and Testing of Anti-neoplastic Compositions

Reagents. Purified phytohemagglutinin (Wellcome Diagnostics, Research Triangle Park, NC); Ficoll-Hypaque (Pharmacia Fine Chemicals, Piscataway, N.J.); human IL-1 (Genzyme, Boston, Mass.): recombinant IPN-$\gamma$ (AMGen, Thousand Oaks, Cal.) human thrombin and bovine serum albumin-linoleic fatty acid conjugate (Sigma, St. Louis, Mo.) were obtained from the supplier.

Antibody MAb 9.3 (Ledbetter et al., J. Immunol. (1985) 135:2331-2336), a specific monoclonal antibody to the T-cell marker p44, was available from Dr. J. Ledbetter (Oncogen, Seattle, Wash.). Bovine TGF-$\beta$1 was purified from spleen and human TGF-$\beta$2 was purified from the conditioned medium of a prostatic adenocarcinoma cell line. Both TGF-$\beta$ preparations were homogeneous by sodium dodecyl sulfate-polacrylamide gel electrophoresis. Oncostatin M (Zarling et al., Proc. Natl. Acad. Sci. USA (1986) 83:9739-9743), isolated from serum-free supernatants of macrophage-like cells was available from Dr. J. Zarling (ONCOGEN, Seattle, Wash.) (see copending application Ser. No. 935,283, filed Nov. 26, 1983 now abandoned and application Ser. No. 811,235, filed Dec. 20, 1985 now abandoned and was quantitated in the assay system described below.

Cells and propagation. All cultures were routinely maintained at 37° C. in a humidified atmosphere of 5% $CO_2$ in Dulbecco's modified Eagle's medium (Grand Island, N.Y.), supplemented with 10% heat-inactivated fetal bovine serum, L-glutamine, and penicillin-streptomycin. The following cell lines were used: A375, A549, NIH 3T3, Mv1Lu, and L929. HTB24 cells were maintained in RPMI 1640 medium (GIBCO, Grand Island, N.Y.), supplemented with 10% fetal bovine serum, L-glutamine and penicillin-streptomycin. (All cell lines are available from the ATCC, Rockville, Md.)

Source of TGF-$\beta$1, IFN-$\gamma$, and Oncostatin M.

Leukofractions, containing monocuclear cells, were separated from buffy coats of blood from normal adult volunteers (Puget Sound Blood Center, Seattle, Wash.). Mononuclear cells were isolated by isopyknic centrifugation with Ficoll-Hypaque. Interface cells were collected and platelets removed with thrombin (0.5 U/mL) in the presence of 1 mM $Ca^{2+}$, $Mg^{2+}$. To deplete monocytes and B-cells, cells adherent to plastic surfaces or nylon wool were removed. The resulting peripheral blood lymphocytes (PBL) consisted of 94% T-cells, fewer than 0.5% B-cells, and 5% monocytes. PBL were activated with phytohemagglutinin (PHA) (2 g/mL) for 96 hours in chemically-defined medium and supplemented with bovine serum albumin-linoleic fatty acid conjugate (200 mg/L). This collection of supernatant fluid was discarded. Following primary activation, non-adherent lymphoblasts were adjusted to $1 \times 10^6$/mL in fresh chemical-defined medium containing bovine serum albumin-linoleic fatty acid conjugate and re-stimulated with PHA (0.5 g/mL) and monoclonal antibody MAb 9.3 (1 μg/mL) at 37° C., 5% $CO_2$ for 72 hours. Seventy-two-hour collections were taken for four weeks. The serum-free conditioned medium was collected, clarified by centrifugation and concentrated by ultrafiltration (Amicon Diaflo membrane YM-10, 10,000 molecular weight cutoff: Amicon Corp., Danvers, Mass.). The concentrated supernatant of activated T-lymphocytes was the starting material for the purification of TGF-$\beta$1, $\gamma$-IFN, and Oncostatin M.

Purification of TGF-$\beta$1, $\gamma$-IFN, and Oncostatin M. The retentate, after ultrafiltration, was dialyzed against 0.1 M acetic acid, and the supernatant after centrifugation, was lyophilized and reconstituted in 6 mL of 1 M acetic acid (50 mg/mL) for subsequent gel permeation chromatography on a column (2.5 × 88 cm) of Bio-Gel P-60 (Bio-Rad Laboratories, Richmond, Cal.) and equilibrated with 1 M acetic acid at 20 mL/hr. Fractions comprising the major growth inhibitory activity were pooled.

Further purification of TGF-$\beta$1, $\gamma$-IFN, and Oncostatin M was achieved by reversed-phase HPLC. The separations were performed on a preparative μ Bondapak $C_{18}$ column (10 μm particle size 7.8 × 300 mm: Waters, Milford, Mass.) at room temperature. The primary mobile phase was 0.05% aqueous trifluoroacetic acid, and the secondary mobile phase was acetonitrile containing 0.045% trifluoroacetic acid. The concentration of acetonitrile was increased linearly (0.083% per min) during 240 min at a flow rate of 2.0 mL/min. at room temperature for elution of proteins.

TGF-$\beta$1-containing fractions were rechromatographed on an analytical μ Bondapak $C_{18}$ column (3.9 × 300 mm) with 1-propanol containing 0.035% trifluoroacetic acid as the mobile-phase modifier. The 1-propanol concentration was increased linearly (0.028% per min) during 6 hours at a flow rate of 0.2 mL/min.

$\gamma$-IFN-containing fractions were rechromatographed on an analytical Bondapak $C_{18}$ column and subsequently on an analytical $C_4$ Vydac column (330-A pore size, The Separations Group, Hesperia, Cal.) with 1-propanol containing 0.035% trifluoroacetic acid for elution. The 1-propanol concentration was increased linearly (0.028% per min) during 360 min at a flow rate of 0.2 mL/min at room temperature for elution of proteins.

Oncostatin M-containing fractions were rechromatographed on an analytical μ Bondapak $C_{18}$ column and subsequently on an analytical $C_4$ Vydac column with 1-propanol containing 0.035% trifluoracetic acid for elution. The gradient conditions and flow rate were the same as described for the purification of $\gamma$-IFN. Purified Oncostatin M was analyzed by sodium dodecylsulfate polyacrylamide gel electrophoresis, and was assayed for growth inhibitory activity on A375 cells and MvlLu cells. Oncostatin M used in synergy experiments was approximately 80% pure. The dose-response and synergy characteristics of this preparation of Oncostatin M were identical to homogenous Oncostatin M isolated from the conditioned medium of macrophage-like cells and purified by reversed-phase HPLC (Zarling et al., Proc. Natl. Acad. Sci. USA (1986) 83:9739–9743).

Growth inhibition assay. A375 melanoma cells ($4 \times 10^3$ cells/50 μl) or MvlLu mink lung epithelial cells ($3.5 \times 10^3$ cells/50 μl) were subcultured for four hours on flat-bottomed 96-well tissue culture plates (Costar 3596, Cambridge, Mass.) in Dulbecco's modified Eagle's medium, supplemented with 10% heat-inactivated fetal bovine serum. Test samples to be assayed for growth inhibition were diluted in medium and assayed in triplicate with 50 μl of the diluted sample added to each well. The cells were incubated for 72 hours at 37° C. At the end of this incubation period, each well was treated for 24 hours with 100 μl of medium containing 5-[$^{125}$I]iodo-2'-deoxyuridine (0.05 μCi/well (Amersham, Arlington Heights, Ill.). The monolayers were washed with phosphate-buffered saline, fixed in 95% methanol, air-dried, and the [$^{125}$I]iododeoxyuridine incorporated by cells was solubilized with 200 μl of 1 N sodium hydroxide. The amount of cell growth was measured by the amount of [$^{125}$I]iododeoxyuridine incorporated into the DNA of actively growing cells. One unit of activity was defined as the amount of inhibitor required to give 50% maximal response relative to untreated cells. Cytostasis was also estimated by incubating unlabeled target cells with serial dilutions of growth inhibitor. After 48 hours, cells were trypsinized and the total number of viable and dead cells was determined by staining with 0.2% trypan blue. A direct correlation between decrease of recoverable viable cells and decrease of incorporated radio-activity into the DNA of viable cells was observed.

Amino acid sequence determination. Automated sequence analyses of unmodified Oncostatin M and peptides derived from IFN-$\gamma$ by cleavage with endoproteinase Lys-C were performed on a Model 470A amino acid sequencer (Applied Biosystems, Foster City, Cal.).

Results

Source of TGF-$\beta$1, IFN-$\gamma$, and Oncostatin M.

TGF-$\beta$1, IFN-$\gamma$, and Oncostatin M were isolated from chemically-defined conditioned medium of activated human T-lymphocytes. Primary T-lymphoblasts could be maintained for up to four weeks by restimulation every third day with PHA and T-cell-specific monoclonal antibody MAb9.3. The supernatant fluids were collected every third day for a four-week period. At the end of the culture period, more than 95% of the cells were still viable. This method of T-lymphocyte propagation yielded a cell population essentially free of monocytes/macrophages and provided a 99% pure T-cell-derived conditioned medium. The initial clarified conditioned medium was concentrated by ultrafiltration using filters of 10,000 molecular weight cutoff.

Purification of TGF-1, IFN-$\gamma$, and Oncostatin M.

Conditioned medium from activated T-cells was found to inhibit the proliferation of A375 melanoma cells. In contrast, neither PHA nor T-cell-specific monoclonal antibody MAb 9.3 nor conditioned medium from resting T-cells affected the proliferation of A375 cells.

The concentrated supernatant from activated T-cells was dialyzed against 0.1 M acetic acid, lyophilized, and the acid-soluble growth inhibitory activity was subjected to gel permeation chromatography on Bio-Gel P-60. The bulk of contaminating protein was eluted in the exclusion volume of the column and was separated from the A375 growth inhibitory activity. A major peak of anti-proliferative activity against A375 cells, with a molecular weight range between $M_r$ 14,000 to 28,000 was found. Fractions with growth inhibitory activity were pooled lyophilized, and further purified by reversed-phase HPLC.

The P-60 pool was reconstituted in 0.05% trifluoroacetic acid in water, and then chromatographed on a μ Bondapak $C_{18}$ column. Three peaks of activity were found to be well resolved from each other. Only 33% of the initial activity was recovered. GIF-1 eluted at 33% acetonitrile and contained 10% of the recovered activity; GIF-2 eluted at 38% acetonitrile, representing 13% of the recovered activity and GIF-3 eluted between 40 and 42% acetonitrile containing approximately 77% of the total recovered activity. The major activity peaks were pooled as indicated and subsequently characterized.

Production of TGF-1 by human T-lymphocytes. GIF-1 affected the growth of certain tumor and normal cell targets. As shown in the following Table 1, the proliferation of Mv1Lu mink lung epithelial cells, A375 melanoma cells, A549 lung carcinoma cell, as well as primary human B-lymphocytes was inhibited following treatment with GIF-1. HTB24 human mammary carcinoma cells did not respond to GIF-1. In contrast, the growth of quiescent NIH-3T3 fibroblast was augmented in the presence of GIF-1.

TABLE I
Effect of GIF-1 on cell growth responses in vitro

| | $ED_{50}$[1] | | |
|---|---|---|---|
| | Inhibition | No Effect | Stimulation |
| Mv1Lu (mink lung epithelium) | 1.7 | — | — |
| A375 (human melanoma) | 10.0 | — | — |
| A549 (human lung carcinoma) | 13.3 | — | — |
| HTB24 (human mammary carcinoma) | — | null | — |
| Primary human B lymphocytes[2] | 1.7 | — | — |
| NIH 3T3 (murine fibroblasts)[3] | — | — | 83.5 |

[1]$ED_{50}$ defined as the effective dose of GIF-1 (standardized in units of A375 growth inhibitory activity/mL) required to give a 50% maximal growth response on the above panel of target cells.
[2]Prepared from PBL and assayed according to Suzuki et al. J. Immunol. (1985) 135:2470.
[3]Assayed in reduced serum concentration (1% FBS).

GIF-1 purified from T-cell conditioned medium and TGF-η1 purified from spleen have almost identical biological activities in stimulation of the growth of NIH 3T3 fibroblasts and inhibition of DNA synthesis in Mv1Lu mink lung cells, suggesting that GIF-1 and TGF-β1 are functionally similar polypeptides. GIF-1, as well as TGF-β1, stimulated growth of NIH 3T3 fibroblasts at 83.5 units/mL, and maximum response at 1000 units/mL (standardized on A375 cells). GIF-1 and TGF-β1 inhibited DNA synthesis in Mv1Lu Cells at 1.7 units/mL, and maximum response at 17 units/mL.

GIF-1 and TGF-1 eluted as symmetrical activity peaks at 22% 1-propanol from a u Bondapak $C_{18}$ column. For comparison, TGF-β2 purified from prostatic adenocarcinoma cells, eluted at 20.5 % 1-propanol under standard conditions. These data demonstrate that GIF-1 and TGF-β1 have similar biological activities and identical chromatographic properties, suggesting that TGF-β1 is produced and released by activated human T-cells.

IFN-γ inhibits the proliferation of A375 melanoma cells. GIF-2 was purified to homogeneity by reversed-phase HPLC with sequentially acetonitrile and 1-propanol as the mobile phase and trifluoroacetic acid as the ionic modifier for elution. Two peaks of growth inhibitory activity were obtained with apparent $M_4$ of 25,000 and 20,000 when analyzed by sodium dodecyl sulfate-polyacrylamide gel electrophoresis. Edman degradation yielded no signal. The sequences of two selected fragments of GIF-2, using the endoproteinase Lys-C for enzymatic cleavage, were subsequently determined, representing residues 69-80 and 95-108 of IFN-γ (Rinderknecht et al., J. Biol. Chem. (1984) 259:6790), respectively. These results suggest that GIF-2 and IFN-γ are structurally similar polypeptides.

Production of Oncostatin M by human T-lymphocytes. The purity of the final GIF-3 preparation was determined by sodium dodecyl sulfate-polyacrylamide gel electrophoresis under reducing conditions. The preparation remained slightly contaminated by a higher molecular weight protein. The major polypeptide band had an $M_4$ of 28,000. Two amino-terminal sequences were determined by automated Edman degradation for the GIF-3 preparation. Unambiguous identification of phenylthiohydantoin derivatives of amino acids was possible up to residue 19 for the major sequence, except at positions 5, 6, 7, 11, 14, and 15. The amino-terminal sequence of GIF-3 read as follows:

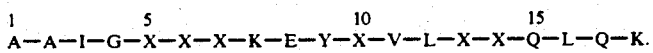

Identified phenylthiohydantoin derivatives of amino acids up to residue 19 were identical with those established for the partial sequence of Oncostatin M (Zarling et al., supra) derived from phorbolester-induced U937 histolytic lymphoma cells.

The final GIF-3 preparation was functionally characterized in selected bioassays. The growth of L924 cells was not affected by Oncostatin M, which argues against contamination by or possible synergy between low levels of TNF-β, TNF-α or natural killer cell cytotoxic factor. Oncostatin M did not demonstrate significant anti-viral effects. This preparation failed to augment IL-2-dependent thymocyte proliferation consistent with the action of IL-1.

A375 melanoma cells were very sensitive to the growth inhibitory activity of GIF-3 and Oncostatin M purified from macrophage-like cells. GIF-3 and Oncostatin M at 40 units/mL inhibited DNA synthesis in A375 cells by 95%. After a 24-hour incubation of A375 cells with 40 units of GIF-3, the number of cells did not significantly differ from the original number at the start of the incubation. When GIF-3 was removed from A375 cells after 24 hours of incubation, these cells continued to grow and had only a slightly reduced ability to incorporate [$^{125}$I]iododeoxyuridine, suggesting that GIF-3 had a cytostatic rather than a cytolytic effect on A375 cells and that GIF-3 action is reversible within the first 24 hours. After a 48-hour incubation of A375 cells with GIF-3 or longer, these cells had irreversibly lost the ability to proliferate.

Cooperative antiproliferative activity of TGF-$\beta$, IFN-$\gamma$, and Oncostatin M on A375 cells. The growth inhibitory activity of highly purified TGF-$\beta$1, rIFN-$\gamma$, and functionally characterized Oncostatin M (GIF-3) on A375 cells was determined, and possible synergy between TGF-$\beta$1 and Oncostatin M, TGF-$\beta$1 and IFN-$\gamma$, and Oncostatin M and IFN-$\gamma$ in inhibiting A375 proliferation was tested. TGF-$\beta$1 is expressed in units of Mv1Lu growth inhibitory activity, or IFN-$\gamma$ (recombinant gamma-interferon) in units of anti-viral activity and Oncostatin M in units of A375 growth inhibitory activity. Concentrations of TGF-$\beta$1 (1 to 30 U/mL) and Oncostatin M (0.5 to 10 U/mL) were chosen which caused either no or only minimal growth inhibition when tested individually. Synergistic responses to simultaneous inhibition with TGF-$\beta$1 and Oncostatin M occurred in all combinations tested, with the degree of enhancement ranging from 2.5 to 3.1 times the expected, additive response. For example, cell proliferation was inhibited approximately 48% by 3.4 U/mL of TGF-1 and 1.8 U/mL of Oncostatin M, which individually inhibited cell growth by 7 and 12%, respectively. The predicted additive effect would be 19%. The actual response measured was 2.5 times higher. To determine whether the antiproliferative activity of TGF-$\beta$1 was truly synergistic with that of Oncostatin M, data from 5 dose combinations were plotted in an isobologram. In this graphic analysis, the observed marked departure of the line connecting the experimental points below the line for additive effect is indicative of synergistic interaction.

A similar matrix of inhibitor concentrations was tested for TGF-$\beta$1 and IFN-$\gamma$. Synergistic responses to simultaneous inhibition with TGF-1 (0.8 to 32 U/mL) and IFN-$\gamma$ (1 to 20 U/ml) were observed. The degree of enhancement was only 1.6 to 1.9 times the expected, additive response. For example, A375 proliferation was inhibited approximately 42% by 8 U/mL of TGF-1 in combination with 2.5 U/mL of IFN-$\gamma$, which individually inhibited cell growth by 8 and 14%, respectively. The predicted additive effect would be 22%. However, a strict additive response in the inhibition of A375 cells was observed at higher concentrations of TGF-$\beta$1 and IFN-$\gamma$. The addition of 32 U/mL of TGF-$\beta$1 and 10 U/mL of IFN-$\gamma$ to A375 cells in combination caused 72% growth inhibition, which individually inhibited cell growth by 37 and 35%, respectively.

An additive antiproliferative response was observed when combinations of Oncostatin M (1 to 5 U/mL) and IFN-$\gamma$ (1 to 10 U/mL) were simultaneously added to A375 cells.

Isolation of TGF-2.

Source of TGP-$\beta$. TGF-$\beta$2 was purified from Tamoxifen-supplemented medium conditioned by a line of human prostatic adenocarcinoma cells, PC-3 (Kaighn et al., *Invest. Urol.* (1979) 17:16–23, derived from a bone metastasis. The PC-3 line was obtained from the American Type Culture Collection (Rockville, Md.). Cells were grown to confluence on 850 sq. cm plastic roller bottles (Corning 25140) in 50 ml of F-12 HAM (Sigma, St. Louis, Mo.) and Dulbecco's modified Eagle's medium (1:1), and supplemented with 10% heat-inactivated fetal bovine serum. The monolayers were washed three times with phosphate-buffered saline. The medium was discarded and replaced with 50 ml of fresh serum-free medium supplemented with Tamoxifen (1-p-R-dimethyl-aminoethoxyphenyl-trans-1,2-diphenylbut-1-ene: Sigma) dissolved in dimethylsulfoxide to reach a final concentration of $1.4 \times 10^{-5}$ M. Serum-free conditioned medium was collected every 48 h for a 6-day period by decantation, clarified by low-speed centrifugation at $1000 \times g$ for 15 min, and passed through a filter with a pore size of 0.45 $\mu$m (Nalgene, Rochester, N.Y.). Aprotinin (3.6 mg/L) and phenylmethanesulfonyl fluoride (10 mg/L) were added to the filtrate.

Batch Adsorption on Methylsilyl-Controlled Pore Glass (MS-CG). PC-3-conditioned medium was acidified to pH 4.0 with concentrated trifluoroacetic acid (TFA). In the batch adsorption procedure, 30 g of MS-CpG (40 um, Sepralyte, Analytichem International, Harbor City, Cal.), previously washed with 100% acetonitrile containing 0.1% TFA, were suspended in 1.6 L of acidified conditioned medium in a vessel equipped with a microcarrier magnetic stirrer (Bellco Glass, Vineland, N.J.). The mixture was stirred for 1 hour at 4° C. The beads were resuspended in 10 volumes of 0.1% TFA and transferred to a column (5.0×3.2 cm) for elution. The column was washed with 200 mL of 0.1% TFA containing 30% acetonitrile and 0.2 M NaCl and batch eluted with 120 mL of 50% acetonitrile, 0.2 M NaCl and 0.1% TFA. The eluate containing TGF-$\beta$2 was dialyzed for 60 h against 0.1 M acetic acid, concentrated by lyophilization and reconstituted in 0.1% TFA containing 40% acetonitrile.

Gel Permeation Chromatography. The supernatant containing TGF-$\beta$2 activity was further purified by gel permeation chromatography on a column (21.5×600 mm) of Bio-Sil TSK-250 (Bio Rad Laboratories, Richmond, Cal.). The column was equilibrated with 0.1% TFA containing 40% acetonitrile at 2 mL/min, at 22° C. 4 mL fractions were collected.

Reversed-Phase High Performance Liquid Chromatography. The final purification of hTGF-$\beta$2 was achieved by reversed-phase HPLC. All separations were performed on a $\mu$Bondapak C$_{18}$ column (10 m particle size, 3.9×300 mm, Waters Associates, Milford, Mass.). A linear acetonitrile gradient composed of 0.05% TFA in water as starting buffer and 0.045% of TFA in acetonitrile as limit buffer was used. The column was operated at a flow rate of 0.2 mL/min at 22° C. The column eluent was collected in 1 mL portions. Pools of fractions comprising the major growth-inhibitory activity were diluted 2-fold with 0.5% TFA and rechromatographed on the same column, previously equilibrated with 0.05% TFA in water. The column was then eluted with a linear 1-propanol gradient containing 0.035% TFA at 0.2 mL/min at 22° C. The column eluent was collected in 1 mL fractions.

Protein Determination. Total protein was determined (Bradford, *Anal. Biochem.* 72:248–254 (1976) using bovine serum albumin as a standard. Protein was also determined by UV-absorbance at 215 nm comparing peak areas with the peak area of a known amount of bovine insulin.

Growth Inhibition Assay. Mv1Lu mink lung epithelial cells (CC1-64, American Type Culture Collection) were subcultured on flat-bottomed 96-well tissue culture plates (Costar 3596, Cambridge Mass.) in 50 uL of complete Dulbecco's modified Eagle's medium, supplemented with 10% heat-inactivated fetal bovine serum at $3.5 \times 10^3$ cells/well. Aliquots from column fractions to be assayed for growth inhibition were diluted in complete medium and assayed in triplicate with 50 μL of the diluted sample added to each well. The cells were incubated for 72 h at 37° C. in a humidified 5% $CO_2$-95% air atmosphere. At the end of this incubation period, each well was treated for 24 h with 100 uL of complete medium containing 5-[$^{125}$I]-iodo-2'-deoxyuridine (0.05 μCi/well, Amersham IM.355V). The monolayers were washed with phosphate-buffered saline, fixed in 95% methanol, and the [$^{125}$I]-IdU incorporated by the cells was solubilized with 200 L of 1N NaOH. The amount of cell growth was measured by the amount of [$^{125}$I]-IdU incorporated into the DNA of actively growing cells. One unit of activity was defined as the amount of TGF-β2 required to give 50% maximal response in the above assay.

NaDodSO$_4$-Polyacrylamide Gel Electrophoresis. NaDodSO$_4$-polyacrylamide gel electrophoresis was performed as described (Laemmli, Nature (1970) 227:680-685). A 12-20% acrylamide gradient slab ($140 \times 120 \times 0.75$ mm) was prepared with a 5% stacking gel. Molecular weight standards were ovalbumin ($M_4 = 43,000$), α-chymotrypsinogen ($M_4 = 25,700$), β-lactoglobulin ($M_4 18,400$), lysozyme ($M_4 = 14,300$), and bovine trypsin inhibitor ($M_4 = 6,200$). After electrophoresis, gels were fixed in 40% methanol, 10% acetic acid overnight, washed in 10% methanol, 5% acetic acid, for 2 h, and stained with silver (Merril et al., Science (1981) 211:1437-1438.

Amino Acid Sequence Determination For aminoterminal sequence analysis, hTGF-β2 (8 μg) was reduced with dithiothreitol (20 mM) in 100 uL of 0.4 M Tris HCl/6 M guanidine-HCl/0.1% Na$_2$EDTA, pH 8.5, for 2 h at 50° C. and subsequently S-pyridylethylated with vinylpyridine (100 mM) for 4 h at 22° C. The reaction mixture was acidified to pH 2.0 with 20% TFA and desalted on an RP-300 column ($2.1 \times 30$ mm, Applied Biosystems, Foster City, Cal.). The concentration of acetonitrile was increased linearly (1%/min) during 1 h at a flow rate of 100 L/min, at 35° C. One symmetrical polypeptide peak was eluted with a gradient of aqueous acetonitrile containing 0.085% TFA.

Automated sequence analysis of S-pyridylethylated TGF-β2 was performed on a model 470A amino acid sequencer (Applied Biosystems) using the 03RPTH program. 3.0 mg of BioBrene Plus (Applied Biosystems) were applied and subjected to three precycles of Edman degradation prior to sample application. Conversion of the thiazolinone derivatives to phenylthiohydantoin amino acids was carried out using 25% TFA. Phenylthiohydantoin amino acid derivatives were separated by reversed-phase HPLC on a PTH-C$_{18}$ column ($2.1 \times 220$ mm, Applied Biosystems) with a sodium acetate buffer/tetrahydrofuran/acetonitrile gradient (Hunkapiller & Hood, Science (1983) 219:650-659), on-line, on a model 120A PTH Analyzer (Applied Biosystems).

RESULTS

Source and Initial Fractionation of hTGF-β2 hTGF-β2 was isolated from Tamoxifen-supplemented, serum-free conditioned medium of the human prostatic adenocarcinoma cell line, PC-3. The quantitation of hTGF-β2 was based on its ability to inhibit DNA synthesis in epithelial mink lung (CC1-64) cells. The amount of hTGF-β2 produced was increased by treatment of PC-3 cells with Tamoxifen. The addition of Tamoxifen to serum-free medium at $1.4 \times 10^5$ M increased the level of secretion of hTGF-2 2-5-fold compared to Tamoxifen-free controls after 6 days of treatment.

The supernatant fluids were collected every other day for a 6-day period. Culture conditions were such that at the end of the culture period more than 90% of the cells were still viable and attached as monolayers. A summary of the steps leading to the isolation of hTGF-β2 and its recovery is presented in Table II.

TABLE II

| Purification of hTGF-β2 from conditioned medium of human prostatic adenocarcinoma cells, PC-3. | | | | | | |
|---|---|---|---|---|---|---|
| Purification step | Volume mL | Protein recovered mg | hTGF-β2 activity recovered Units | Relative specific activity Units/μg | Degree of purification —fold | Recovery % |
| 1. PC-3-conditioned medium | 1600 | 686 | $3.5 \times 10^6$ | 5.1 | 1 | 100 |
| 2. Eluate from MS-CpG | 220 | 50 | $3.1 \times 10^6$ | 62 | 12 | 89 |
| 3. Bio-Sil TSK-250 | 12 | 2.3 | $2.9 \times 10^6$ | 1260 | 250 | 83 |
| 4. μBondapak C$_{18}$ (acetonitrile) | 7 | 0.340 | $2.8 \times 10^6$ | 8240 | 1620 | 80 |
| 5. μBondapak C$_{18}$ (1-propanol) | 6 | 0.035 | $2.6 \times 10^6$ | 74300 | 14600 | 74 |

Batch adsorption on MS-C$_p$G at 20 g/L of acidified PC-3-conditioned medium removed all detectable growth-inhibitory activity present in the medium. After the adsorption step, the silica-based adsorbent was transferred to a column and washed with 30% acetonitrile containing 0.2 M NaCl and 0.1% TFA. Some adsorbed protein was removed, but the growth-inhibitory activity was still retained by the support. Elution with 50% acetonitrile containing 0.2 M NaCl and 0.1% TFA removed the bound hTGF-2 from the support. Typically, about 50 mg of protein was recovered per preparation with a reduction in volume of about 8-fold and with a yield close to 90% of the initial growth-inhibitory activity.

Purification of hTGF-β2. Dialysis of the MS-CPG eluate against acetic acid, lyophilization and subsequent gel permeation chromatography of the acid-soluble partially purified hTGF-β2 resulted in 83% recovery of the initial growth-inhibitory activity. One peak of activity was found with an $M_4 = 14,000$ (ribonuclease A; $M_4$ 13,700). hTGF-β2-containing fractions were pooled to provide 2.3 mg protein, diluted 2-fold with 0.05% TFA, and further purified by reversed-phase HPLC. Growth-inhibitory activity of individual fractions was determined. hTGF-β2 was well separated from the bulk of contaminating protein which eluted at lower and higher concentrations of organic solvent. Fractions N54-58 were pooled, diluted 2-fold with 0.05% TFA, and taken for rechromatography. A 7-fold purification of hTGF-Rβ2 after gel permeation chromatography was obtained. 80% of the initial growth-inhibitory activity was recovered (Table II).

Rechromatography of hTGF-Rβ2-containing fractions on $C_{18}$ support and elution with a linear 1-propanol gradient containing 0.035% TFA separated a well-defined peak of activity from the bulk of UV-absorbing material. The growth-inhibitory activity copurified with a distinct absorbance peak at 20.8% 1-propanol. Fractions were pooled and further analyzed. The purification of hTFG-β2 was approximately 15,000-fold with a yield of 74% of the initial total growth-inhibitory activity. The overall recovery of hTGF-2 per step was 89-96%. The highest specific activity observed was $74 \times 10^6$ units/mg, which gives half-maximal activity in the range of $5 \times 10^{-12}$ M.

Characterization of hTGF-β2. The purity of the final hTGF-β2 preparation was determined by analytical NaDodSO₄-polyacrylamide gel electrophoresis and compared with TGF-β1 isolated from bovine spleen. One major polypeptide band, with an $M_4 = 24,000$, was observed under nonreducing conditions. When samples were electrophoresed under reducing conditions, the polypeptide stained as a single band at $M_4 = 13,000$.

Materials—Human TGF-β2 was isolated from tamoxifen-supplemented, serum-free medium conditioned by the human prostatic adenocarcinoma cell line PC3 and purified.

Sequencer reagents were obtained from Applied Biosystems: solvents for rpHPLC were from Burdick and Jackson. CNBr was from Kodak: 4-vinylpyridine was from Aldrich Chemical Co.; S-(4-pyridylethyl)cysteine was from Sigma: all other chemicals were reagent grade. Endoproteinase Lys-C was from Boehringer Mannheim; *Staphylococcus aureus* V8 protease was obtained from Miles Laboratories; L-(tosylamido-2-phenyl)ethyl chloromethyl ketone-treated trypsin was from Worthington.

S-pyridylethylation—For reduction, TGF-β2 was reduced with dithiothreitol (20 mM) in 100 μl of 0.4 M Tris-HCl buffer, pH 8.5, containing 6 M guanidine HCl, 0.1% Na₂ EDTA, for 2 h at 50° C. and subsequently S-pyridylethylated with 4-vinylpyridine (100 mM) for 4 h at 22° C. The reaction mixture was acidified to pH 2.0 with 20% TFA and desalted by rpHPLC.

Enzymatic cleavages—Cleavage with endoproteinase Lys-C was done in 40 μl of 0.1 M Tris-acetic acid buffer, pH 8.0, at 37° C. for 24 h. The enzyme/substrate ratio was 1 to 10 (wt/wt). *S. aureus* V8 protease cleavage was done in a similar manner at an enzyme/substrate ratio of 1 to 10 at 37° C. for 20 h. Trypsin digestion of peptide K 38-94 was done in 40 μl of 0.1 M Tris-acetic acid buffer, pH 8.0, containing 30% acetonitrile, at 37° C. for 20 h. The enzyme/substrate ratio was 1 to 10. The enzymatic digests were acidified with 20% TFA to pH 2.0 and separated by rpHPLC.

Chemical cleavage—For CNBr cleavage at methionyl residues, 300 pmol of S-pyridylethylated TGF-Rβ2 was applied onto the glass fiber sample filter of the gas-phase sequencer. The filter was saturated with 30 μl of a solution containing 15 mg CNBr in 100 μl of 70% (v/v) formic acid and then placed in a vacuum desiccator and left over CNBr/70% formic acid vapor for 20 h at room temperature. (March et al., *Nature* (1985) 315:641-647: Simpson and Nice, *Biochemistry Internat.* (1984) 8:787-791). The sample was then air-dried at 44° C. for 20 min.

Peptide purification—Peptide purification by rpHPLC was performed on a Model 130A separation system (Applied Biosystems) and carried out at 35° C. on an RP-300 column (2.1×300 mm; *Applied Biosystems*). Linear acetonitrile gradients composed of 0.1% TFA in water as starting buffer and acetonitrile containing 0.085% TFA as limiting buffer were employed for elution. Peptides were collected manually. Endoproteinase Lys-C peptides (38-94; 98-107; 108-110), trypsin peptides (61-94), and *S. aureus* V8 protease peptides (172-99) could be used for sequence analysis without further purification.

Amino acid analysis—Dried samples were gas-phase hydrolyzed with constant boiling HCl (Pierce) containing 5% thioglycolic acid (Sigma) under reduced pressure and flushed with $N_2$ in a Teflon-sealed glass hydrolysis bulb (Pierce) at 105° C. for 24 h. The hydrolysates were dried in a Speedvac centrifugal concentrator (Savant Instruments) and derivatized with phenyl-isothiocyanate (Pierce) for 20 min at room temperature. Phenylthiocarbamyl amino acid derivatives were analyzed by rpHPLC on a PICO TAG column (39×150 mm; Waters Associates) with a sodium acetate-triethylamine buffer, pH 5.80/acetonitrile gradient, at 37° C., using essentially the procedure outlined by Waters Associates. Data collection and reduction were performed on an 840 Data Module (Waters Associates).

Amino acid sequence analysis—Automated sequence analysis was performed on a Model 470A amino acid sequencer (Applied Biosystems) with the 03RPTH program. A total of 1.5 mg of BioBrene Plus (Applied Biosystems) was applied and subjected to three precycles of Edman degradation prior to sample application. Conversion of the thiazolinone derivatives to phenylthiohydantoin amino acids separated by rpHPLC on a PTH C18 column (2.1×220 mm; Applied Biosystems) with a sodium acetate-trimethylamine buffer, containing 3.5% tetrahydrofuran/acetonitrile gradient as outlined by Applied Biosystems, on-line, on a Model 120A PTH analyzer (Applied Biosystems).

Results of Enzymatic Cleavage of TGF-β2 and Peptide Purification

S-pyridylethylated TGF-β2 (250 pmol) was digested with the endoproteinase Lys-C. The presence of Na dodecylsulfate was required to completely solubilize the modified TGF-β2 derivative. The enzyme digest was acidified to pH 2.0 with TFA and the peptides separated by rpHPLC. Aliquots of peptide-containing fractions were taken for sequence analysis. The complete sequences of the listed peptides were determined, all containing a carboxyl-terminal lysine, consistent with the enzyme specificity. Sequence analysis of peak A revealed the sequences of K 1-25 and K 38-94. Edman degradation of K 38-94 in pool B allowed assignment of the first 29 residues from positions 39 through 66 of TGF-2. Peptide K 111-112 was not retained by the RP-300 column. No attempt was made to sequence the peptide. A complex rpHPLC pattern was obtained. Na dodecylsulfate interacts with the peptides to be separated as well as the reversed-phase column support to behave like an ion exchanger, leading to peak broadening and peak splitting.

Peak B, containing K 38-94, and possibly partially cleaved peptides with the same amino-terminal sequence, was pooled, dried, and subfragmented with trypsin. The digest was acidified to pH 2.0 with TFA and the peptides separated by rpHPLC. The amino-terminal sequence of peptide T 61-94 was determined, which allowed assignment of the first 31 residues from position 61 through 91 of TGF-β2.

For cleavage at the carboxyl of glutamic acid, S-pyridylethylated TGF-β2 (200 pmol) was digested with S. aureus V8 protease, at pH 8.0 in the presence of 0.1% Na dodecylsulfate. The enzyme digest was acidified and peptides purified by rpHPLC. Pool B was diluted 2-fold with 0.1% TFA and rechromatographed on the same column using the same gradient conditions. Peptide E 72-99 of TGF-β2 was subjected to automated Edman degradation and was sequenced in its entirety, containing a carboxyl-terminal glutamic acid which is consistent with the enzyme specificity.

Chemical cleavage of TGF-β2

S-pyridylethylated TGF-μ2 (33 pmol) was cleaved with CNBr at the single methionine residue. Sequence analysis of the mixture of peptides CB1-104 and CB105-112 confirmed the assignments made for positions 105 through 110 in the amino-terminal Edman degradation of T 98-107 and T 108-110, and extended the known structure of TGF-β2 to position 112. Peptide CB105-112 did not contain a carboxyl-terminal homoserine and was thus assumed to be the carboxyl-terminal peptide of TGF-β2. Cleavage (approximately 5% of the input TGF-β2) at tryptophan 32 and 52 with excess CNBr (Ozols and Gerard, *J. Biol. Chem.* (1977) 252;5986-5989) yielded 2 minor identifiable sequences.

The amino acid sequence is given below and compared with the amino acid sequence of hTGF-β1.

```
            1         5         10        15        20
hTGF-β1    A L D T N Y C F S S T E K N C C V R Q L
hTGF-β2    A L D A A Y C F R N V Q D N C C L R P L 25        30        35        40
hTGF-β1    Y I D F R K D L G W K W I H E P K G Y H
hTGF-β2    Y I D F K R D L G W K W I H E P K G Y N 45        50        55        60
hTGF-β1    A N F C L G P C P Y I W S L D T Q Y S K
hTGF-β2    A N F C A G A C P Y L W S S D T Q H S R 65        70        75        80
hTGF-β1    V L A L Y N Q H N P G A S A A P C C V P
hTGF-β2    V L S L Y N T I N P E A S A S P C C V S 85        90        95        100
hTGF-β1    Q A L E P L P I V Y Y V G R K P K V E Q
hTGF-β2    Q D L E P L T I L Y Y I G K T P K I E Q 105       110
hTGF-β1    L S N M I V R S C K C S
hTGF-β2    L S N M I V K S C K C S
```

It is evident from the above results, that by using combinations of various growth regulatory materials, particularly Oncostatin M in conjunction with growth factors, such as transforming growth factors or γ-Interferons, or active analogs or fragments thereof, substantially reduced dosages of the individual compositions may be employed, while still retaining growth modulating effect. In particular, where dosages of TGF-β or γ-interferon are unable to completely inhibit proliferation, when used with Oncostatin M at levels below total inhibiting activity, substantially total inhibition of proliferation is achieved. The compositions can, therefore, be used in the regulation of cell proliferation both in vivo and in vitro, such as in culture, leukophoresis, for prophylactic and therapeutic purposes in vivo, and the like. In addition, a novel TGF is provided, namely TGF-β2 which may be used in conjunction with the other materials to provide for growth regulating activity.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A neoplastic cell proliferation inhibiting composition comprising a cell proliferation inhibiting amount of Oncostatin M in combination with an adjunctive agent consisting of at least one of interferon-γ, transforming growth factor in a physiologically acceptable carrier.

2. A composition according to claim 1, wherein said Oncostatin M is at least 25 weight percent of the inhibiting combination.

* * * * *